United States Patent
Schweizer et al.

(10) Patent No.: US 8,609,153 B2
(45) Date of Patent: *Dec. 17, 2013

(54) CANOLA PROTEIN ISOLATE

(75) Inventors: Martin Schweizer, Winnipeg (CA); Brent E. Green, Warren (CA); Kevin I. Segall, Winnipeg (CA); Randy Willardsen, Roseville, CA (US)

(73) Assignee: Burcon Nutrascience (MB) Corp., Winnipeg, Manitoba (CA)

( * ) Notice: Subject to any disclaimer, the term of this patent is extended or adjusted under 35 U.S.C. 154(b) by 0 days.

This patent is subject to a terminal disclaimer.

(21) Appl. No.: 12/737,085

(22) PCT Filed: Jun. 20, 2009

(86) PCT No.: PCT/CA2009/000855
§ 371 (c)(1), (2), (4) Date: Apr. 25, 2011

(87) PCT Pub. No.: WO2009/152620
PCT Pub. Date: Dec. 23, 2009

(65) Prior Publication Data
US 2011/0200720 A1    Aug. 18, 2011

Related U.S. Application Data

(63) Continuation-in-part of application No. 12/213,499, filed on Jun. 20, 2008, now Pat. No. 7,981,450.

(51) Int. Cl.
*A61K 36/00* (2006.01)
(52) U.S. Cl.
USPC .......................................... 424/725; 424/776
(58) Field of Classification Search
None
See application file for complete search history.

(56) References Cited

U.S. PATENT DOCUMENTS

| | | |
|---|---|---|
| 2004/0039174 A1 | 2/2004 | Barker et al. |
| 2004/0254353 A1 | 12/2004 | Barker et al. |
| 2005/0249828 A1 | 11/2005 | Logie et al. |
| 2006/0121171 A1 * | 6/2006 | Schweizer et al. ............ 426/590 |
| 2007/0065567 A1 | 3/2007 | Segall et al. |
| 2008/0125577 A1 | 5/2008 | Gosnell et al. |

FOREIGN PATENT DOCUMENTS

| | | |
|---|---|---|
| WO | WO02/089597 | 11/2002 |
| WO | WO03/088760 | 10/2003 |

OTHER PUBLICATIONS

Berot, S. et al. Large scale purification of rapeseed proteins (*Brassica napus* L). J. Chromatography B, 818:35-42, Aug. 26, 2004.
Bhatty, R.S. et al. 1968, The proteins of rapeseed (*Brassica napus* L). soluble in salt solutions. Can. J. Biochem., 46:1191-1197.
Gehrig P.M. et al. 1996 Proc. Natl. Acad. Sci. U.S.A., 93:3647-3652.
Krzyzaniak et al. 1998 Nahrung (42), Nr. 3/4, p. 201-204.
Monsalve R.I. et al. 1990 J. Exper. Bot., 42(222):89-94.
Muren E. et al. 1996 Eur. J. Biochem., 242: 214-219.

* cited by examiner

*Primary Examiner* — Terry A McKelvey
*Assistant Examiner* — Randall Winston
(74) *Attorney, Agent, or Firm* — Michael I. Stewart; Sim & McBurney

(57) ABSTRACT

A novel canola protein isolate consisting predominantly of 2S canola protein and having equal to better solubility properties and improved clarity properties in aqueous media, has an increased proportion of 2S canola protein and a decreased proportion of 7S canola protein. The novel canola protein isolate is formed by isoelectric precipitation of aqueous supernatant from canola protein micelle formation and precipitation, to effect precipitation of 7S protein which is sedimented and removed.

15 Claims, 2 Drawing Sheets

CANOLA PROTEIN ISOLATE

REFERENCE TO RELATION APPLICATIONS

This application is a U.S. National Phase filing under 35 USC 371 of PCT/CA2009/000855 filed Jun. 20, 2009 claiming priority under 35 USC 119(e) from U.S. patent application Ser. No. 12/213,499 filed Jun. 20, 2008.

FIELD OF INVENTION

The present invention relates to the production of a novel canola protein isolate and its use in aqueous solutions, including soft drinks and sports drinks.

BACKGROUND TO THE INVENTION

Canola oil seed protein isolates having protein contents of at least 100 wt % (N×6.25) can be formed from oil seed meal by a process as described in copending U.S. patent application Ser. No. 10/137,391 filed May 3, 2002 (U.S. patent application Publication No. 2003-0125526 and WO 02/089597) and U.S. patent application Ser. No. 10/476,230 filed Jun. 9, 2004 (U.S. patent application Publication No. 2004-0254353), assigned to the assignee hereof and the disclosures of which are incorporated herein by reference. The procedure involves a multiple step process comprising extracting canola oil seed meal using an aqueous salt solution, separating the resulting aqueous protein solution from residual oil seed meal, increasing the protein concentration of the aqueous solution to at least about 200 g/L while maintaining the ionic strength substantially constant by using a selective membrane technique, diluting the resulting concentrated protein solution into chilled water to cause the formation of protein micelles, settling the protein micelles to form an amorphous, sticky, gelatinous, gluten-like protein micellar mass (PMM), and recovering the protein micellar mass from supernatant having a protein content of at least about 100 wt % (N×6.25). As used herein, protein content is determined on a dry weight basis. The recovered PMM may be dried.

In one embodiment of the process, the supernatant from the PMM settling step is processed to recover canola protein isolate from the supernatant. This procedure may be effected by initially concentrating the supernatant using an ultrafiltration membrane and drying the concentrate. The resulting canola protein isolate has a protein content of at least about 90 wt %, preferably at least about 100 wt % (N×6.25).

The procedures described in U.S. patent application Ser. Nos. 10/137,391 and 10/476,230 are essentially batch procedures. In copending U.S. patent application Ser. No. 10/298,678 filed Nov. 19, 2002 (U.S. patent application Publication No. 2004-0039174 and WO 03/043439), assigned to the assignee hereof and the disclosures of which are incorporated herein by reference, there is described a continuous process for making canola protein isolates. In accordance therewith, canola oil seed meal is continuously mixed with an aqueous salt solution, the mixture is conveyed through a pipe while extracting protein from the canola oil seed meal to form an aqueous protein solution, the aqueous protein solution is continuously conveyed through a selective membrane operation to increase the protein content of the aqueous protein solution to at least about 50 g/L, while maintaining the ionic strength substantially constant, the resulting concentrated protein solution is continuously mixed with chilled water to cause the formation of protein micelles, and the protein micelles are continuously permitted to settle while the supernatant is continuously overflowed until the desired amount of PMM has accumulated in the settling vessel. The PMM is recovered from the settling vessel and may be dried. The PMM has a protein content of at least about 90 wt % (N×6.25), preferably at least about 100 wt %. The overflowed supernatant may be processed to recover canola protein isolate therefrom, as described above.

Canola seed is known to contain about 10 to about 30 wt % proteins and several different protein components have been identified. These proteins include a 12S globulin, known as cruciferin, a 7S protein and a 2S storage protein, known as napin. As described in copending U.S. patent application Ser. No. 10/413,371 filed Apr. 15, 2003 (U.S. patent application Publication No. 2004-0034200 and WO 03/088760) and U.S. patent application Ser. No. 10/510,766 filed Apr. 29, 2005 (US Patent Application Publication No. 2005-0249828), assigned to the assignee hereof and the disclosures of which are incorporated herein by reference, the procedures described above, involving dilution of concentrated aqueous protein solution to form PMM and processing of supernatant to recover additional protein, lead to the recovery of isolates of different protein profiles.

In this regard, the PMM-derived canola protein isolate has a protein component content of about 60 to about 98 wt % of 7S protein, about 1 to about 15 wt % of 12S protein and 0 to about 25 wt % of 2S protein. The supernatant-derived canola protein isolate has a protein component content of about 60 to about 95 wt % of 2S protein, about 5 to about 40 wt % of 7S protein and 0 to about 5 wt % of 12S protein. Thus, the PMM-derived canola protein isolate is predominantly 7S protein and the supernatant-derived canola protein isolate is predominantly 2S protein. As described in the aforementioned U.S. patent application Ser. Nos. 10/413,371 and 10/510,766, the 2S protein has a molecular size of about 14,000 daltons, the 7S protein has a molecular mass of about 145,000 daltons and the 12S protein has a molecular size of about 290,000 daltons.

There has previously been described in Krzyzaniak et al in Nahrung (42) 1998, Nr. 3/4, p. 201-204, the purification to homogenity of the 2S storage protein napin from rape seed and characterization of the secondary structure and conformation stability of the protein. The napin was isolated by extraction from rape seeds with buffer A (50 mM $NaH_2PO_4$, pH 7.0, 1 mM EDTA), followed by precipitation using $(NH_4)_2SO_4$, dissolution of the resulting pellet in buffer A, dialysis against the same buffer and desalting by gel chromatography using a Sephadex G-50 column. Fractions containing napin extract were collected and re-precipitated with $(NH_4)_2SO_4$. The resulting crude napin was dissolved in buffer B (buffer A at pH 7.4), dialyzed against it, then loaded on to a CM-Sephadex C-50 column and eluted with a gradient of 0.15 to 0.35 M NaCl in buffer B. Fractions containing napin were pooled, precipitated with $(NH_4)_2SO_4$, redissolved in buffer A and dialyzed. Napin was further purified by cation exchange HPLC using gradients up to 1 M NaCl at pH 5.0. The fractions with $\lambda_{max}$=280 nm were collected, concentrated and analyzed.

The applicants are aware of additional literature references describing the laboratory preparation of samples of 2S canola protein, purified to homogeneity, as follows:

Berot, S., Compoint, J. P., Larre, C., Malabat, C. and Gueguen, J. 2005. Large scale purification of rapeseed proteins (*Brassica napus* L). J. Chromatography B, 818: 35-42.

Bhatty, R. S., McKenzie, S. L. and Finlayson, A. J. 1968. The proteins of rapeseed (*Brassica napus* L.) soluble in salt solutions. Can. J. Biochem., 46:1191-1197.

Gehrig, P. M., Krzyzaniak, A., Barciszewski, J. and Biemann, K. 1996. Mass spectrometric amino acid sequencing of a mixture of seed storage proteins (napin) from *Brassica napus*, products of a multigene family. Proc. Natl. Acad. Sci. U.S.A., 93: 3647-3652.

Monsalve, R. I. and Rodriguez, R. 1990. Purification and characterization of proteins from the 2S fraction from seeds of the Brassicaceae family. J. Exper. Bot., 41(222): 89-94.

Muren, E., Ek, B., Bjork, I. and Rask, L. 1996. Structural comparison of the precursor and the mature form of napin, the 2S storage protein in *Brassica napus*. Eur. J. Biochem., 242: 214-219.

The novel canola protein isolates provided herein are distinguished from such disclosures in that the 2S predominated canola protein isolates provided herein always comprise a small quantity of 7S protein.

Canola is also known as rapeseed or oil seed rape.

SUMMARY OF INVENTION

It has now surprisingly been found that a novel canola protein isolate, having an increased proportion of 2S protein, preferably containing at least about 85 wt % of 2S protein, and having a reduced proportion of 7S protein, exhibits superior properties in aqueous solution to the supernatant-derived canola protein isolate prepared following the procedure of the aforementioned U.S. patent application Ser. Nos. 10/137,391 and 10/476,230.

In addition to equal or greater solubility at a variety of pH values, the novel canola protein isolate provided herein is able to provide improved clarity in solution with soft drinks and sports drinks, providing clear protein fortified beverages. Further, the novel canola protein isolate exhibits a greater solubility than the supernatant-derived canola protein isolate at a pH of about 3.5 in about 0.1M sodium chloride solution.

In one aspect of the present invention, there is provided a canola protein isolate consisting predominantly of 2S canola protein having a protein content of at least about 90 wt % (N×6.25), preferably at least about 100 wt %, on a dry weight basis (d.b.) and having an increased proportion of 2S canola protein and a decreased proportion of 7S canola protein when compared to canola protein isolates consisting predominantly of 2S canola protein and derived from aqueous supernatant from canola protein micelle formation and precipitation. The canola protein isolate is derived by isoelectric precipitation of 7S protein from the supernatant.

The novel canola protein isolate and composition of the present invention possess a number of unique properties, different from those of the supernatant derived canola protein isolate and include solubility, clarity, heat stability, absorbance at 280 nm, surface hydrophobicity and amino acid profile. These properties are described below and the data supporting this discussion appear in the Examples below.

Solubility:

The novel canola protein isolate exhibits the same or increased solubility in water and in carbonated and non-carbonated soft drinks and sport drinks in comparison to supernatant-derived canola protein isolate over a wide range of pH and at about 1% w/v protein concentration.

In addition, the novel canola protein isolates exhibits the same or increased solubility in water over a wide range of pH and at an about 1% w/v protein concentration, wherein, following formation of the solutions or dispersions, the samples are centrifuged to sediment insoluble material and yield a clear supernatant.

Further, the novel canola protein isolate exhibits greater solubility in 0.1M sodium chloride solution at pH 3.5 in comparison to supernatant-derived canola protein isolate.

Clarity:

The novel canola protein isolate may be incorporated into a variety of beverages, including carbonated and non-carbonated soft drinks as well as juices, punches and cocktails, to provide protein fortification to such beverages. Such beverages have a wide range of pH values, ranging from about 2.5 to about 5, and often are packaged in 12 fluid ounce quantities. The novel canola protein isolate may be added in any convenient quantity to provide protein fortification to the beverage, for example, at least about 5 g of the novel canola protein isolate per 12 fluid ounce quantity.

The added novel canola protein isolate dissolves in the beverage and does not impair the clarity of the beverage. In a clear beverage at a protein concentration of 2 wt %, the clarity is less than about 0.5 when determined by measuring the absorbance of visible light at 600 nm. In water at a protein concentration of 1 wt %, the clarity is less than about 1.0 over a pH range of about 2 to about 7, when determined by measuring the absorbance of visible light at 600 nm.

Heat Stability:

The novel canola protein isolate of the invention has improved heat stability both at pH 6 and 7 in comparison to supernatant-derived canola protein isolate. Following isoelectric precipitation of 7S protein from the supernatant, as described in detail below, the heat-treated supernatant is resistant to further protein deposition upon heating.

Absorbance at 280 nm:

The novel canola protein of the invention has weaker absorbance at 280 nm than the supernatant-derived canola protein isolate. This result indicates that the novel canola protein isolate of the invention contains less tyrosine and tryptophan, which absorb strongly at 280 nm, than supernatant-derived canola protein.

Surface Hydrophobicity:

The novel canola protein isolate of the invention has a lower surface hydrophobicity than supernatant-derived canola protein isolate, probably arising from the lower globulin content of the novel canola protein isolate compared to the supernatant-derived canola protein isolate.

The surface hydrophobicity of the novel canola protein isolate is generally less than about 25, preferably less than about 20.

The novel canola protein isolate of the invention is prepared by isoelectric precipitation of 7S protein from the concentrated supernatant from the procedure of U.S. patent application Ser. Nos. 10/137,391 and 10/476,230 in order to reduce the proportion of 7S protein in the concentrated supernatant and hence to increase the proportion of 2S protein. Alternatively, the treatment may be carried out on the supernatant prior to concentration or following partial concentration of the supernatant. Accordingly, in another aspect of the present invention, there is provided a process for the preparation of a canola protein isolate having an increased proportion of 2S canola protein, which comprises (a) providing an aqueous solution of 2S and 7S proteins consisting predominantly of 2S protein, (b) isoelectrically precipitating 7S canola protein from the aqueous solution, (c) removing precipitated 7S protein from the aqueous solution, and (d) recovering a canola protein isolate having a protein content of at least about 90 wt % (N×6.25) d.b. and having an increased proportion of 2S canola protein compared to the aqueous solution of 2S and 7s proteins.

GENERAL DESCRIPTION OF INVENTION

Figure 1:
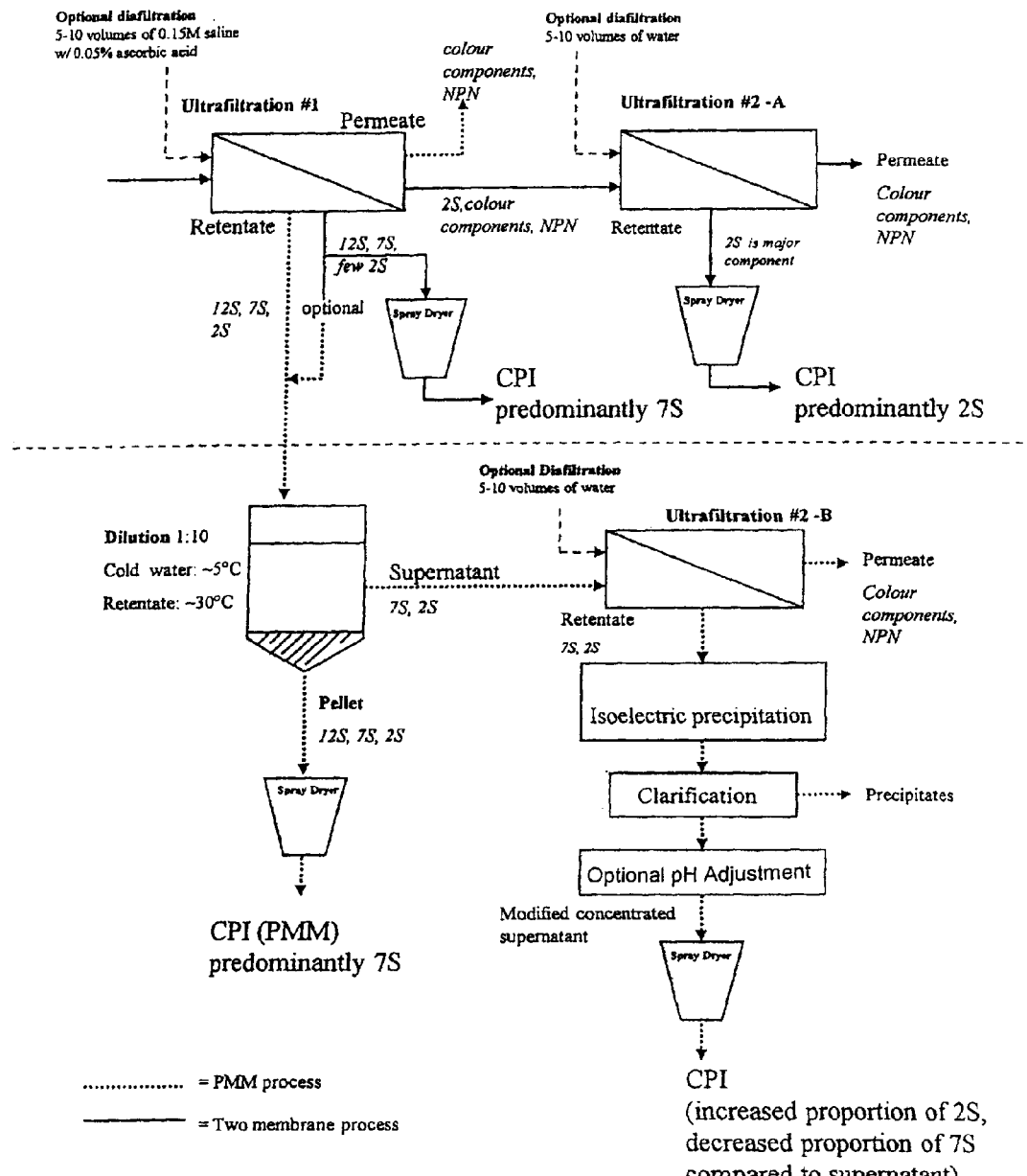
FIG. 1 is a schematic representation of a protein isolate recovery process.

The novel canola protein isolate provided herein has a protein content of at least about 90 wt % (N×6.25), preferably at least about 100 wt %, and may be isolated from canola oil seed meal by a batch process, or a continuous process, or a semi-continuous process.

The novel canola protein isolate provided herein consists predominantly of 2S protein and has an increased proportion of 2S canola protein and a decreased proportion of 7S canola protein when compared to canola protein isolates consisting predominantly of 2S protein and derived from supernatant from canola protein micelle formation and precipitation and prepared under the same experimental conditions of preparation. As set forth above, the novel canola protein isolates of the invention, while having a decreased proportion of 7S protein and an increased proportion of 2S protein, there is always present a small residual quantity of 7S protein. The canola protein isolate is derived by isoelectric precipitation of 7S protein from the supernatant.

The novel canola protein isolates contain at least about 85 wt % of 2S canola protein and less than about 15 wt % of 7S canola protein, preferably at least about 90 wt % of 2S canola protein and less than about 10 wt % of 7S canola protein and more preferably as great a proportion of 2S protein as is possible. As noted above, such canola protein isolate may be obtained by treatment of supernatant, partially concentrated supernatant and concentrated supernatant, as described in more detail below. The treatment of the supernatant, partially concentrated supernatant and concentrated supernatant causes precipitation of the 7S protein, which can be removed from the treated supernatant by any convenient means, such as centrifugation or filtration. The 2S protein is not affected by the treatment and hence the treatment increases the proportion of 2S protein present by decreasing the proportion of 7S protein.

The novel canola protein isolate is soluble in aqueous solution over a wide range of pH values, generally about pH 2 to about pH 7.5, preferably about 2 to about 4, generally having solubility equal to or greater than canola protein isolate consisting predominantly of 2S protein and derived from supernatant from canola protein micelle formation and precipitation under the same experimental conditions of preparation. In addition, aqueous solutions of the novel canola protein isolate in soft drinks, including both carbonated and non-carbonated soft drinks and sports drinks, including both carbonated and non-carbonated sports energy drinks, such as those commercially-available, have a greater clarity than such aqueous solutions produced from canola protein isolate consisting predominantly of 2S protein and derived from supernatant from canola protein micelle formation and precipitation under the same conditions of preparation.

The concentration of canola protein isolate in the aqueous solution, including solution in soft drinks and sports drinks, may vary depending on the intended use of the solution. In general, the protein concentration may vary from about 0.1 to about 30 wt %, preferably about 1 to about 5 wt %.

Accordingly, the present invention includes aqueous solutions of the novel canola protein isolate provided herein, including not only those mentioned above, but also other beverages, such as juices, alcoholic beverages, coffee-based beverages and dairy-based beverages.

The initial step of the process of providing canola protein isolates involves solubilizing proteinaceous material from canola oil seed meal. The proteinaceous material recovered from canola seed meal may be the protein naturally occurring in canola seed or the proteinaceous material may be a protein modified by genetic manipulation but possessing characteristic hydrophobic and polar properties of the natural protein. The canola meal may be any canola meal resulting from the removal of canola oil from canola oil seed with varying levels of non-denatured protein, resulting, for example, from hot hexane extraction or cold oil extrusion methods. The removal of canola oil from canola oil seed usually is effected as a separate operation from the protein isolate recovery procedure described herein.

Protein solubilization is effected most efficiently by using a food grade salt solution since the presence of the salt enhances the removal of soluble protein from the oil seed meal. Where the canola protein isolate is intended for non-food uses, non-food-grade chemicals may be used. The salt usually is sodium chloride, although other salts, such as, potassium chloride, may be used. The salt solution has an ionic strength of at least about 0.05, preferably at least about 0.10, to enable solubilization of significant quantities of protein to be effected. As the ionic strength of the salt solution increases, the degree of solubilization of protein in the oil seed meal initially increases until a maximum value is achieved. Any subsequent increase in ionic strength does not increase the total protein solubilized. The ionic strength of the food grade salt solution which causes maximum protein solubilization varies depending on the salt concerned and the oil seed meal chosen.

In view of the greater degree of dilution required for protein precipitation with increasing ionic strengths, it is usually preferred to utilize an ionic strength value less than about 0.8, and more preferably a value of about 0.1 to about 0.15.

In a batch process, the salt solubilization of the protein is effected at a temperature of from about 5° C. to about 75° C., preferably accompanied by agitation to decrease the solubilization time, which is usually about 10 to about 60 minutes. It is preferred to effect the solubilization to extract substantially as much protein from the oil seed meal as is practicable, so as to provide an overall high product yield.

The lower temperature limit of about 5° C. is chosen since solubilization is impractically slow below this temperature while the upper preferred temperature limit of about 75° C. is chosen due to the denaturation temperature of some of the present proteins.

In a continuous process, the extraction of the protein from the canola oil seed meal is carried out in any manner consistent with effecting a continuous extraction of protein from the canola oil seed meal. In one embodiment, the canola oil seed meal is continuously mixed with a food grade salt solution and the mixture is conveyed through a pipe or conduit having a length and at a flow rate for a residence time sufficient to effect the desired extraction in accordance with the parameters described herein. In such continuous procedure, the salt solubilization step is effected rapidly, in a time of up to about 10 minutes, preferably to effect solubilization to extract substantially as much protein from the canola oil seed meal as is practicable. The solubilization in the continuous procedure is effected at temperatures between about 5° C. and about 75° C., preferably between about 15° C. and about 35° C.

The aqueous food grade salt solution generally has a pH of about 5 to about 6.8, preferably about 5.3 to about 6.2, the pH of the salt solution may be adjusted to any desired value within the range of about 5 to about 6.8 for use in the extraction step by the use of any convenient acid, usually hydrochloric acid, or alkali, usually sodium hydroxide, as required.

The concentration of oil seed meal in the food grade salt solution during the solubilization step may vary widely. Typical concentration values are about 5 to about 15% w/v.

The protein extraction step with the aqueous salt solution has the additional effect of solubilizing fats which may be present in the canola meal, which then results in the fats being present in the aqueous phase.

The protein solution resulting from the extraction step generally has a protein concentration of about 5 to about 40 g/L, preferably about 10 to about 30 g/L.

The aqueous salt solution may contain an antioxidant. The antioxidant may be any convenient antioxidant, such as sodium sulfite or ascorbic acid. The quantity of antioxidant employed may vary from about 0.01 to about 1 wt % of the solution, preferably about 0.05 wt %. The antioxidant serves to inhibit oxidation of phenolics in the protein solution.

The aqueous phase resulting from the extraction step then may be separated from the residual canola meal, in any convenient manner, such as by employing a decanter centrifuge, followed by disc centrifugation and/or filtration to remove residual meal. The separated residual meal may be dried for disposal.

The colour of the final canola protein isolate can be improved in terms of light colour and less intense yellow by the mixing of powdered activated carbon or other pigment adsorbing agent with the separated aqueous protein solution and subsequently removing the adsorbent, conveniently by filtration, to provide a protein solution. Diafiltration also may be used for pigment removal.

Such pigment removal step may be carried out under any convenient conditions, generally at the ambient temperature of the separated aqueous protein solution, employing any suitable pigment adsorbing agent. For powdered activated carbon, an amount of about 0.025% to about 5% w/v, preferably about 0.05% to about 2% w/v, is employed.

Where the canola seed meal contains significant quantities of fat, as described in U.S. Pat. Nos. 5,844,086 and 6,005,076, assigned to the assignee hereof and the disclosures of which are incorporated herein by reference, then the defatting steps described therein may be effected on the separated aqueous protein solution and on the concentrated aqueous protein solution discussed below. When the colour improvement step is carried out, such step may be effected after the first defatting step.

As an alternative to extracting the oil seed meal with an aqueous salt solution, such extraction may be made using water alone, although the utilization of water alone tends to extract less protein from the oil seed meal than the aqueous salt solution. Where such alternative is employed, then the salt, in the concentrations discussed above, may be added to the protein solution after separation from the residual oil seed meal in order to maintain the protein in solution during the concentration step described below. When a first fat removal step is carried out, the salt generally is added after completion of such operations.

Another alternative procedure is to extract the oil seed meal with the food grade salt solution at a relatively high pH value above about 6.8, generally up to about 9.9. The pH of the food grade salt solution may be adjusted to the desired alkaline value by the use of any convenient food-grade alkali, such as aqueous sodium hydroxide solution. Alternatively, the oil seed meal may be extracted with the salt solution at a relatively low pH below about pH 5, generally down to about pH 3. Where such alternative is employed, the aqueous phase resulting from the oil seed meal extraction step then is separated from the residual canola meal, in any convenient manner, such as by employing decanter centrifugation, followed by disc centrifugation and/or filtration to remove residual meal. The separated residual meal may be dried for disposal.

The aqueous protein solution resulting from the high or low pH extraction step then is pH adjusted to the range of about 5 to about 6.8, preferably about 5.3 to about 6.2, as discussed above, prior to further processing as discussed below. Such pH adjustment may be effected using any convenient acid, such as hydrochloric acid, or alkali, such as sodium hydroxide, as appropriate.

The aqueous protein solution is concentrated to increase the protein concentration thereof while maintaining the ionic strength thereof substantially constant. Such concentration generally is effected to provide a concentrated protein solution having a protein concentration of at least about 50 g/L, preferably at least about 200 g/L, more preferably at least about 250 g/L.

The concentration step may be effected in any convenient manner consistent with batch or continuous operation, such as by employing any convenient selective membrane technique, such as ultrafiltration or diafiltration, using membranes, such as hollow-fibre membranes or spiral-wound membranes, with a suitable molecular weight cut-off, such as about 3,000 to about 100,000 daltons, preferably about 5,000 to about 10,000 daltons, having regard to differing membrane materials and configurations, and, for continuous operation, dimensioned to permit the desired degree of concentration as the aqueous protein solution passes through the membranes.

As is well known, ultrafiltration and similar selective membrane techniques permit low molecular weight species to pass through the membrane while preventing higher molecular weight species from so doing. The low molecular weight species include not only the ionic species of the food grade salt but also low molecular weight materials extracted from the source material, such as, carbohydrates, pigments and anti-nutritional factors, as well as any low molecular weight forms of the protein. The molecular weight cut-off of the membrane is usually chosen to ensure retention of a significant proportion of the protein in the solution, while permitting contaminants to pass through having regard to the different membrane materials and configurations.

The concentrated protein solution then may be subjected to a diafiltration step using an aqueous salt solution of the same molarity and pH as the extraction solution. Such diafiltration may be effected using from about 2 to about 20 volumes of diafiltration solution, preferably about 5 to about 10 volumes of diafiltration solution. In the diafiltration operation, further quantities of contaminants are removed from the aqueous protein solution by passage through the membrane with the permeate. The diafiltration operation may be effected until no significant further quantities of contaminants and visible colour are present in the permeate. Such diafiltration may be effected using the same membrane as for the concentration step. However, if desired, the diafiltration step may be effected using a separate membrane with a different molecular weight cut-off, such as a membrane having a molecular weight cut-off in the range of about 3,000 to about 100,000 daltons, preferably about 5,000 to about 10,000 daltons, having regard to different membrane materials and configuration.

An antioxidant may be present in the diafiltration medium during at least part of the diafiltration step. The antioxidant may be any convenient antioxidant, such as sodium sulfite or ascorbic acid. The quantity of antioxidant employed in the diafiltration medium depends on the materials employed and may vary from about 0.01 to about 1 wt %, preferably about 0.05 wt %. The antioxidant serves to inhibit oxidation of phenolics present in the concentrated canola protein isolate solution.

The concentration step and the diafiltration step may be effected at any convenient temperature, generally about 20° to about 60° C., preferably about 20 to about 30° C., and for the period of time to effect the desired degree of concentration. The temperature and other conditions used to some degree depend upon the membrane equipment used to effect the concentration and the desired protein concentration of the solution.

The concentrated and optionally diafiltered protein solution may be subject to a further defatting operation, if required, as described in U.S. Pat. Nos. 5,844,086 and 6,005,076.

The concentrated and optionally diafiltered protein solution may be subject to a colour removal operation as an alternative to the colour removal operation described above. Powdered activated carbon may be used herein as well as granulated activated carbon (GAC). Another material which may be used as a colour adsorbing agent is polyvinyl pyrrolidone.

The colour adsorbing agent treatment step may be carried out under any convenient conditions, generally at the ambient temperature of the canola protein solution. For powdered activated carbon, an amount of about 0.025% to about 5% w/v, preferably about 0.05% to about 2% w/v, may be used. Where polyvinylpyrrolidone is used as the colour adsorbing agent, an amount of about 0.5% to about 5% w/v, preferably about 2% to about 3% w/v, may be used. The colour adsorbing agent may be removed from the canola protein solution by any convenient means, such as by filtration.

The concentrated and optionally diafiltered protein solution resulting from the optional colour removal step may be subjected to pasteurization to kill any bacteria which may have been present in the original meal as a result of storage or otherwise and extracted from the meal into the canola protein solution in the extraction step. Such pasteurization may be effected under any desired pasteurization conditions. Generally, the concentrated and optionally diafiltered protein solution is heated to a temperature of about 55° to about 70° C., preferably about 60° to about 65° C., for about 10 to about 15 minutes, preferably about 10 minutes. The pasteurized concentrated protein solution then may be cooled for further processing as described below, preferably to a temperature of about 25° to about 40° C.

Depending on the temperature employed in the concentration step and optional diafiltration step and whether or not a pasteurization step is effected, the concentrated protein solution may be warmed to a temperature of at least about 20°, and up to about 60° C., preferably about 25° to about 40° C., to decrease the viscosity of the concentrated protein solution to facilitate performance of the subsequent dilution step and micelle formation. The concentrated protein solution should not be heated beyond a temperature above which micelle formation does not occur on dilution by chilled water.

The concentrated protein solution resulting from the concentration step, and optional diafiltration step, optional colour removal step, optional pasteurization step and optional defatting step, then is diluted to effect micelle formation by mixing the concentrated protein solution with chilled water having the volume required to achieve the degree of dilution desired. Depending on the proportion of canola protein desired to be obtained by the micelle route and the proportion from the supernatant, the degree of dilution of the concentrated protein solution may be varied. With lower dilution levels, in general, a greater proportion of the canola protein remains in the aqueous phase.

When it is desired to provide the greatest proportion of the protein by the micelle route, the concentrated protein solution is diluted by about 5 fold to about 25 fold, preferably by about 10 fold to about 20 fold.

The chilled water with which the concentrated protein solution is mixed has a temperature of less than about 15° C., generally about 1° to about 15° C., preferably less than about 10° C., since improved yields of protein isolate in the form of protein micellar mass are attained with these colder temperatures at the dilution factors used.

In a batch operation, the batch of concentrated protein solution is added to a static body of chilled water having the desired volume, as discussed above. The dilution of the concentrated protein solution and consequential decrease in ionic strength causes the formation of a cloud-like mass of highly associated protein molecules in the form of discrete protein droplets in micellar form. In the batch procedure, the protein micelles are allowed to settle in the body of chilled water to form an aggregated, coalesced, dense, amorphous sticky gluten-like protein micellar mass (PMM). The settling may be assisted, such as by centrifugation. Such induced settling decreases the liquid content of the protein micellar mass, thereby decreasing the moisture content generally from about 70% by weight to about 95% by weight to a value of generally about 50% by weight to about 80% by weight of the total micellar mass. Decreasing the moisture content of the micellar mass in this way also decreases the occluded salt content of the micellar mass, and hence the salt content of dried isolate.

Alternatively, the dilution operation may be carried out continuously by continuously passing the concentrated protein solution to one inlet of a T-shaped pipe, while the diluting water is fed to the other inlet of the T-shaped pipe, permitting mixing in the pipe. The diluting water is fed into the T-shaped pipe at a rate sufficient to achieve the desired degree of dilution of the concentrated protein solution.

The mixing of the concentrated protein solution and the diluting water in the pipe initiates the formation of protein micelles and the mixture is continuously fed from the outlet from the T-shaped pipe into a settling vessel, from which, when full, supernatant is permitted to overflow. The mixture preferably is fed into the body of liquid in the settling vessel in a manner which minimizes turbulence within the body of liquid.

In the continuous procedure, the protein micelles are allowed to settle in the settling vessel to form an aggregated, coalesced, dense, amorphous, sticky, gluten-like protein micellar mass (PMM) and the procedure is continued until a desired quantity of the PMM has accumulated in the bottom of the settling vessel, whereupon the accumulated PMM is removed from the settling vessel. In lieu of settling by sedimentation, the PMM may be separated continuously by centrifugation.

The combination of process parameters of concentrating of the protein solution to a preferred protein content of at least about 200 g/L and the use of a dilution factor of about 10 to about 20, result in higher yields, often significantly higher yields, in terms of recovery of protein in the form of protein micellar mass from the original meal extract, and much purer isolates in terms of protein content than achieved using any of the known prior art protein isolate forming procedures discussed in the aforementioned US patent applications.

By the utilization of a continuous process for the recovery of canola protein isolate as compared to the batch process, the initial protein extraction step can be significantly reduced in time for the same level of protein extraction and significantly higher temperatures can be employed in the extraction step. In addition, in a continuous operation, there is less chance of contamination than in a batch procedure, leading to higher product quality and the process can be carried out in more compact equipment.

The settled isolate is separated from the residual aqueous phase or supernatant, such as by decantation of the residual aqueous phase from the settled mass or by centrifugation. The PMM may be used in the wet form or may be dried, by any convenient technique, such as spray drying or freeze drying, to a dry form. The dry PMM has a high protein content, in excess of about 90 wt % protein, preferably at least about 100 wt % protein (calculated as Kjeldahl N×6.25), and is substantially undenatured (as determined by differential scanning calorimetry). The dry PMM isolated from fatty oil seed meal also has a low residual fat content, when the procedures of U.S. Pat. Nos. 5,844,086 and 6,005,076 are employed as necessary, which may be below about 1 wt %.

As described in the aforementioned U.S. patent application Ser. Nos. 10/412,371 and 10/510,766, the PMM consists predominantly of a 7S canola protein having a protein component content of about 60 to 98 wt % of 7S protein, about 1 to about 15 wt % of 12S protein and 0 to about 25 wt % of 2S protein.

The supernatant from the PMM formation and settling step contains significant amounts of canola protein, not precipitated in the dilution step, and is processed to recover canola protein isolate therefrom. As described in the aforementioned U.S. patent application Ser. Nos. 10/413,371 and 10/510,766, the canola protein isolate derived from the supernatant consists predominantly of 2S canola protein having a protein component content of about 60 to about 95 wt % of 2S protein, about 5 to about 40 wt % of a 7S protein and 0 to about 5 wt % of 12S protein.

The supernatant from the dilution step, following removal of the PMM, is concentrated to increase the protein concentration thereof. Such concentration is effected using any convenient selective membrane technique, such as ultrafiltration, using membranes with a suitable molecular weight cut-off permitting low molecular weight species, including the salt and other non-proteinaceous low molecular weight materials extracted from the protein source material, to pass through the membrane, while retaining canola protein in the solution. Ultrafiltration membranes having a molecular weight cut-off of about 3,000 to 100,000 daltons, preferably about 5,000 to about 10,000 daltons, having regard to differing membrane materials and configuration, may be used. Concentration of the supernatant in this way also reduces the volume of liquid required to be dried to recover the protein. The supernatant generally is concentrated to a protein concentration of at least about 50 g/L, preferably about 100 to about 300 g/L, more preferably about 200 to about 300 g/L, prior to drying. Such concentration operation may be carried out in a batch mode or in a continuous operation, as described above for the protein solution concentration step.

The concentrated supernatant then may be subjected to a diafiltration step using water, saline or acidified water. Such diafiltration may be effected using from about 2 to about 20 volumes of diafiltration solution, preferably about 5 to about 10 volumes of diafiltration solution. In the diafiltration operation, further quantities of contaminants are removed from the aqueous supernatant by passage through the membrane with the permeate. The diafiltration operation may be effected until no significant further quantities of contaminants and visible colour are present in the permeate. Such diafiltration may be effected using the same membrane as for the concentration step. However, if desired, the diafiltration may be effected using a separate membrane, such as a membrane having a molecular weight cut-off in the range of about 3,000 to about 100,000 daltons, preferably about 5,000 to about 10,000 daltons, having regard to different membrane materials and configuration.

An antioxidant may be present in the diafiltration medium during at least part of the diafiltration step. The antioxidant may be any convenient antioxidant, such as sodium sulfite or ascorbic acid. The quantity of antioxidant employed in the diafiltration medium depends on the materials employed and may vary from about 0.01 to about 1 wt %, preferably about 0.05 wt %. The antioxidant serves to inhibit oxidation of phenolics present in the concentrated canola protein isolate solution.

The concentrated and optionally diafiltered protein solution may be subject to a colour removal operation as an alternative to the colour removal operation described above. Powdered activated carbon may be used herein as well as granulated activated carbon (GAC). Another material which may be used as a colour adsorbing agent is polyvinyl pyrrolidone.

The colour adsorbing agent treatment step may be carried out under any convenient conditions, generally at the ambient temperature of the canola protein solution. For powdered activated carbon, an amount of about 0.025% to about 5% w/v, preferably about 0.05% to about 2% w/v, may be used. Where polyvinylpyrrolidone is used as the colour adsorbing agent, an amount of about 0.5% to about 5% w/v, preferably about 2% to about 3% w/v, may be used. The colour adsorbing agent may be removed from the canola protein solution by any convenient means, such as by filtration.

In accordance with the present invention, the concentrated and optionally diafiltered supernatant, following the optional colour removal operation, is treated to decrease the quantity of the 7S protein present in the solution by isoelectric precipitation and removal of the 7S protein and thereby increasing the proportion of 2S protein in the canola protein present in the concentrated supernatant.

Such treatment may be effected under pH and salt conditions sufficient to decrease the proportion of 7S present in the concentrated supernatant, preferably to reduce the proportion of 7S protein by a significant extent. In general, the 7S protein content of the supernatant is reduced by at least about 50 wt %, preferably at least about 75 wt % by the treatment. The precipitated 7S protein may be removed in any convenient manner, such as centrifugation or filtration or a combination thereof.

In the isoelectric treatment procedure, a salt, usually sodium chloride, although other salts such as potassium chloride may be used, first is added to the supernatant, partially concentrated supernatant or concentrated supernatant to provide a salinated solution having a conductivity of at least about 0.3mS, preferably about 10 to about 20 mS.

The pH of the salinated supernatant is adjusted to a value to cause isoelectric precipitation of 7S protein, generally to a pH of about 2.0 to about 4.0, preferably about 3.0 to about 3.5. The isoelectric precipitation of the 7S protein may be effected over a wide temperature range, generally from about 5° C. to about 70° C., preferably about 10° C. to about 40° C. The precipitated 7S protein is removed from the isoelectrically precipitated supernatant by any convenient means, such as centrifugation or filtration or a combination thereof.

The isoelectrically precipitated supernatant, if not already concentrated, then is concentrated as discussed above and diafiltered to remove the salt, prior to drying the concentrated and diafiltered supernatant to form the canola protein isolate of the invention. The concentrated, diafiltered and isoelectrically precipitated supernatant may be filtered to remove residual particulates and subjected to an optional colour removal step, as discussed above, prior to drying by any convenient technique, such as spray drying or freeze drying, to a dry form to provide a canola protein isolate according to the present invention. Such canola protein isolate has a high protein content, in excess of about 90 wt %, preferably at least about 100 wt % protein (N×6.25)

The pH of the concentrated, diafiltered and isoelectrically precipitated supernatant may be adjusted prior to drying, to a pH corresponding to the intended use of the dried isolate, generally a pH of about 2 to about 5, preferably about 2.5 to about 4.

Such novel canola protein isolate contains a high proportion of 2S protein, preferably at least 90 wt % and most preferably at least about 95 wt %, of the canola protein in the isolate. There is also a proportion of 7S protein in the isolate.

Alternatively, the isoelectric treatment of the supernatant to precipitate 7S protein may be effected on the supernatant prior to the concentration and diafiltration steps mentioned above. Following removal of the deposited 7S protein, the supernatant then is concentrated, optionally diafiltered, optionally submitted to a colour removal operation, and dried to provide the canola protein isolate according to the invention.

As a further alternative, the supernatant first may be partially concentrated to any convenient level. The partially concentrated supernatant then is subjected to the isoelectric treatment to precipitate 7S protein. Following removal of the precipitated 7S protein, the supernatant is further concentrated, generally to a concentration of about 50 to about 300 g/L, preferably about 200 to about 300 g/L, optionally diafiltered, optionally submitted to a colour removal operation, and dried to provide the canola protein isolate according to the invention.

Precipitated 7S protein is removed from the supernatant, partially concentrated supernatant or concentrated supernatant by any convenient means, such as centrifugation or filtration or a combination thereof.

Following removal of precipitated 7S protein, the isoelectrically treated supernatant or partially concentrated, isoelectrically treated supernatant may be pH adjusted at any point during or after concentration or diafiltration, as discussed above.

DESCRIPTION OF PREFERRED EMBODIMENTS

Referring to FIG. 1, there is shown therein a two-membrane process in comparison to the formation of canola protein isolates (CPIs) by the micelle route.

As can be seen, retentate from a first ultrafiltration stage (Ultrafiltration #1), which may comprise ultrafiltration and diafiltration steps, is processed in one of two ways. In the two-membrane process, the retentate is spray dried to provide a canola protein isolate which consists predominantly of 7S canola protein.

In the procedure of the aforementioned U.S. patent application Ser. Nos. 10/137,321 and 10/476,230, the retentate is passed to a dilution step in which canola protein isolate is precipitated as a protein micellar mass. The protein micellar mass is spray dried to provide a canola protein isolate consisting predominantly of 7S canola protein.

In the two-membrane embodiment, the permeate from the first ultrafiltration step is subjected to a second ultrafiltration step (Ultrafiltration #2-A), which may include ultrafiltration and diafiltration. The retentate from the second ultrafiltration step is spray dried to provide a canola protein isolate consisting predominantly of 2S protein.

In the procedure of U.S. Ser. No. 10/137,321 and U.S. Ser. No. 10/476,230, the supernatant from the precipitation of the protein micellar mass is subjected to an ultrafiltration step (Ultrafiltration #2-B), which may include ultrafiltration and diafiltration. The retentate from the ultrafiltration step is subjected to an isoelectric precipitation of 7S protein and then is spray dried to provide a canola protein isolate consisting predominantly of the 2S protein.

Figure 2:
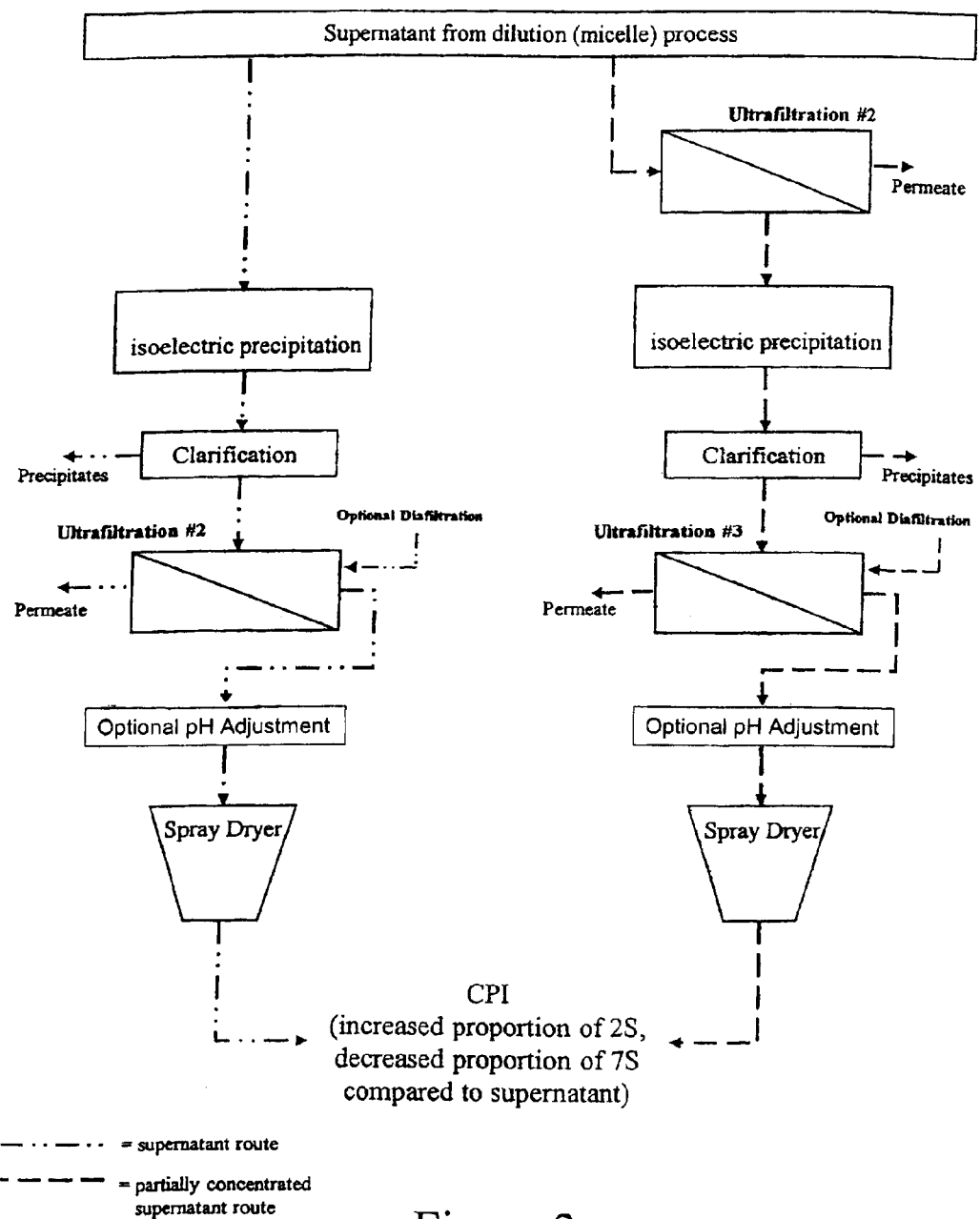
FIG. 2 is a schematic representation of the procedure which is used to produce the novel canola protein isolate of the present invention from the supernatant from the PMM-forming process shown in FIG. 1.

Referring to FIG. 2, there is shown therein procedures for processing the supernatant from the micelle process to produce the novel canola protein isolate of the invention wherein isoelectric precipitation of the supernatant is effected, either following concentration (Ultrafiltration #2) (right-hand flow) or prior to concentration (left-hand flow).

EXAMPLES

Example 1

This Example describes one procedure for the production of a novel canola protein isolate.

An 'a' kg of canola meal was added to 'b' L of 0.1 M NaCl solution at ambient temperature and agitated for 30 minutes to provide an aqueous protein solution. The residual canola meal was removed and the resulting protein solution was clarified by centrifugation and filtration to produce 'c' L of filtered protein solution having a protein content of 'd' % by weight.

A 'e' L aliquot of the protein extract solution was reduced in volume to 'f' L by concentration on a polyvinylidene difluoride (PVDF) membrane having a molecular weight cut-off of 5,000 daltons and then diafiltered with 'g' L of 0.1M NaCl solution on the same membrane. The diafiltered retentate was then pasteurized at 60° C. for 10 minutes. The resulting pasteurized concentrated protein solution had a protein content of 'h' % by weight.

The concentrated solution at 'i'° C. was diluted 'j' into cold RO water having a temperature 'k'° C. A white cloud formed immediately and was allowed to settle. The upper diluting water was removed and the precipitated, viscous, sticky mass (PMM) was recovered from the bottom of the vessel in a yield of 'l' wt % of the filtered protein solution. The dried PMM derived protein was found to have a protein content of 'm' % (N×6.25) d.b. The product was given a designation 'n' C300.

The parameters 'a' to 'n' for two runs are set forth in the following Table I:

TABLE I

| n | BW-SA034-J12-04A | BW-SA035-J14-04A |
|---|---|---|
| a | 15 | 15 |
| b | 150 | 150 |
| c | 75 | 68 |
| d | 1.93 | 1.95 |
| e | 75 | 68 |
| f | 4 | 4 |
| g | 20 | 20 |
| h | 19.08 | 14.20 |
| i | 33 | 33 |
| j | 1:10 | 1:10 |
| k | 3 | 3 |
| l | 37.45 | 28.32 |
| m | 103.08 | 99.73 |

The removed supernatant was reduced in volume to 'o' L by ultrafiltration using a polyethersulfone (PES) membrane having a molecular weight cut-off of 10,000 daltons and then the concentrate was diafiltered on the same membrane with 'p' L of water. The diafiltered concentrate was then pasteurized at 60° C. for 10 minutes. The pasteurized concentrate contained 'q' % protein by weight. With the additional protein recovered from the supernatant, the overall protein recovery of the filtered protein solution was 'r' wt %. The pasteurized concentrate was split into two equal portions. One portion was spray dried to form a final product given designation 'n' C200 and had a protein content of 's' % (N×6.25) d.b.

The parameters 'n' to 's' for two runs are set forth in the following Table II:

TABLE II

| n | BW-SA034-J12-04A | BW-SA035-J14-04A |
|---|---|---|
| o | 3.5 | 3 |
| p | 7 | 6 |
| q | 4.83 | 4.30 |
| r | 49.35 | 38.05 |
| s | 91.73 | 93.69 |

The other portion of the pasteurized, concentrated supernatant was heated to 85° C. for 10 minutes and then centrifuged to remove precipitated protein. The resulting concentrate was then spray dried to form a final product given designation 'n'C200H and had a protein content of 't' % (N×6.25). The parameters 'n' and 't' for two runs are set forth in the following Table III:

TABLE III

| n | BW-SA034-J12-04A | BW-SA035-J14-04A |
|---|---|---|
| t | 91.32 | 92.11 |

Example 2

This Example describes an alternative procedure for the production of a novel canola protein isolate.

Canola meal was added to sodium chloride solution at ambient temperature and agitated for 30 minutes to provide an aqueous protein solution. The residual canola meal was removed and the resulting protein was clarified by centrifugation and filtration.

An aliquot of the protein extract solution was reduced in volume by concentration on a polyvinylidene difluoride (PVDF) membrane and then optionally diafiltered with sodium chloride solution on the same membrane. The retentate was then pasteurized at 60° C. for 10 minutes.

The concentrated solution was diluted into cold RO water. A white cloud formed immediately and was allowed to settle. The upper diluting water was removed and the precipitated, viscous, sticky mass (PMM) was recovered either by decantation or by centrifugation. The PMM was spray dried to form a final product.

Heat treatment was then carried out on the removed diluting water (termed the supernatant), partially concentrated supernatant or concentrated supernatant.

In the case where the heat treatment was carried out on the concentrated supernatant, 'a' L of the supernatant was reduced in volume to 'b' L by ultrafiltration using a polyethersulfone (PES) membrane having a molecular weight cut-off of 'c' Daltons and then the concentrate was diafiltered on the same membrane with 'd' L of water. The diafiltered concentrate was then pasteurized at 60° C. for 10 minutes. The pasteurized concentrate contained 'e' % protein by weight. With the additional protein recovered from the supernatant, the overall protein recovery of the filtered protein solution was 'f' wt %. The pasteurized concentrate was split into two portions. One portion of 'g' L was spray dried to form a final product given designation 'h' C200 and had a protein content of 'i' % (N×6.25) d.b.

The parameters 'a' to 'i' for six runs are set forth in the following Table IV:

TABLE IV

| h | BW-SA033-E10-04A | BW-MS034-E04-05A | BW-SD061-K07-05A | BW-SD062-L18-05A | BW-SD061-I26-06A | BW-SD062-K20-06A |
|---|---|---|---|---|---|---|
| a | 755 | 36 | 33 | 451 | n/a | n/a |
| b | 38 | 2.9 | 4.5 | 45 | n/a | n/a |
| c | 100,000 | 10,000 | 10,000 | 10,000 | n/a | n/a |
| d | 0 | 7 | 23.5 | 225 | n/a | n/a |
| e | 15.2 | 5.7 | 6.18 | 8.73 | n/a | n/a |
| f | 53.7 | 51.8 | 66.7 | 58.4 | n/a | n/a |
| g | 38 | 1.45 | 0 | 0 | n/a | n/a |
| i | 97.12 | 95.23 | n/a | n/a | n/a | n/a |

The other portion of 'j' L of the pasteurized concentrated supernatant was heated to 85° C. for 10 minutes and then centrifuged to remove precipitated protein. The resulting centrate was then spray dried to form a final product given designation 'h' C200H and had a protein content of 'k' % (N×6.25) d.b. The parameters 'h', 'j' and 'k' for six runs are set forth in the following Table V:

TABLE V

| h | BW-SA033-E10-04A | BW-MS034-E04-05A | BW-SD061-K07-05A | BW-SD062-L18-05A | BW-SD061-I26-06A | BW-SD062-K20-06A |
|---|---|---|---|---|---|---|
| j | 0 | 1.45 | 4.5 | 45 | n/a | n/a |
| k | n/a | 92.9 | 95.49 | 96.86 | n/a | n/a |

In the case where the heat treatment was carried out on the supernatant or partially concentrated supernatant, 'l' L of supernatant was reduced in volume to 'm' L by ultrafiltration using a polyethersulfone (PES) membrane having a molecular weight cut-off of 'n' Daltons. The supernatant or partially concentrated supernatant was then heated to 85° C. for 10 minutes and then centrifuged to remove precipitated protein. When necessary, residual precipitated protein was removed by filtration. The clarified sample was then reduced in volume to 'o' L by ultrafiltration using a polyethersulfone (PES) membrane having a molecular weight cut-off of 'p' Daltons. The concentrate contained 'q' % protein by weight. With the additional protein recovered from the supernatant, the overall protein recovery of the filtered protein solution was 'r' wt %. The concentrate was spray dried to form a final product given designation 'h' C200HS and had a protein content of 's' % (N×6.25) d.b. The parameters 'h' and 'l' to 's' for six runs are set forth in the following Table VI:

TABLE VI

| h | BW-SA033-E10-04A | BW-MS034-E04-05A | BW-SD061-K07-05A | BW-SD062-L18-05A | BW-SD061-I26-06A | BW-SD062-K20-06A |
|---|---|---|---|---|---|---|
| l | n/a | n/a | n/a | n/a | 670 | 908 |
| m | n/a | n/a | n/a | n/a | 670 | 228 |
| n | n/a | n/a | n/a | n/a | n/a | 10,000 |
| o | n/a | n/a | n/a | n/a | 26.4 | 25.6 |
| p | n/a | n/a | n/a | n/a | 10,000 | 10,000 |
| q | n/a | n/a | n/a | n/a | 11.6 | 12.57 |
| r | n/a | n/a | n/a | n/a | 59.3 | 57.5 |
| s | n/a | n/a | n/a | n/a | 92.38 | 92.42 | trate was diafiltered on the same membrane with "f" L of acidified water. The diafiltered concentrate was filtered to remove any residual precipitated protein. An aliquot of "g" kg was spray dried to form a final product given designation "h" C200IS, which had a protein content of "i" wt % (N×6.25) d.b.

The parameters "a" to "i" are set forth in the following Table VIII:

TABLE VIII

| h | BW-SA077-K07-07A |
|---|---|
| a | 111.2 |
| b | 0.65 |
| c | 95 |
| d | 7 |
| e | 10,000 |
| f | 30 |
| g | 4 |
| i | 92.86 |

Example 3

This Example describes the production of a novel canola protein isolate in accordance with one embodiment of the invention.

Canola meal was added to sodium chloride solution at ambient temperature and agitated for 30 minutes to provide an aqueous protein solution. The residual canola meal was removed and the resulting protein solution was clarified by centrifugation and filtration.

An aliquot of the protein extract solution was reduced in volume by concentration on a polyethersulfone (PES) membrane. The retentate was then pasteurized at 60° C. for 1 minute.

The concentrated solution was diluted into cold RO water. A white cloud formed immediately. The precipitated, viscous, sticky mass (PMM) was separated from the supernatant by centrifugation. The PMM was spray dried to form a final product.

"a" L of supernatant was combined with "b" kg of sodium chloride to adjust the salt concentration to about 0.1 M. Following salt addition, the pH was adjusted to 3.5 by adding dilute hydrochloric acid. The conductivity of the sample was 14.03 mS. The sample was allowed to rest for 10 minutes as protein precipitation occurred.

The precipitated protein was removed by centrifugation from the acidified supernatant. The precipitated protein was spray dried to form a final product.

The pH of the acidified supernatant was lowered to 3 by the addition of dilute hydrochloric acid. "c" L acidified supernatant was then reduced in volume to about "d" L by ultrafiltration using a polyethersulfone (PES) membrane having a molecular weight cut-off of "e" Daltons and then the concen- Example 4

This Example contains an evaluation of the solubility of the spray dried canola protein isolates produced in Examples 2 and 3.

The solubility of the spray dried concentrated supernatant (C200) and modified products (C200H and C200HS) produced by the procedures of Example 2 and isoelectrically precipitated supernatant (C200IS) produced by the procedures of Example 3, was determined using a modified version of the procedure of Morr et al., J. Food. Sci. 50:1715-1718.

Sufficient protein powder to supply 0.5 g of protein was weighed into a beaker and then a small amount of reverse osmosis (RO) purified water was added and the mixture stirred until a smooth paste formed. Additional water was then added to bring the volume to approximately 45 ml. The contents of the beaker were then slowly stirred for 60 minutes using a magnetic stirrer. The pH was determined immediately after dispersing the protein and was adjusted to the appropriate level (2, 3, 4, 5, 6 or 7) with NaOH or HCl. A sample was also prepared at native pH. For the pH adjusted samples, the pH was measured and corrected two times during the 60 minutes stirring. After the 60 minutes of stirring, the sample was made up to 50 ml total volume with RO water, yielding a 1% w/v protein dispersion. An aliquot of the protein dispersion was reserved for protein content determination by Leco analysis using a Leco FA28 Nitrogen Determinator. Another portion of the sample was centrifuged at 8000 g for 10 minutes. This sedimented any undissolved material and yielded a clear supernatant. The protein content of the supernatant was then determined by Leco analysis.

Solubility(%)=(Supernatant protein conc./Original dispersion protein conc.)×100

The results obtained are set forth in the following Table IX:

TABLE IX

| | | Solubility (%) | | | | | | |
|---|---|---|---|---|---|---|---|---|
| Batch | Product | pH 2 | pH 3 | pH 4 | pH 5 | pH 6 | pH 7 | Native pH |
| SA033-E10-04A | Concentrated supernatant (C200) | 86.5 | 86.7 | 91.7 | 97.2 | 81.2 | 75.6 | 89.8 |
| MS043-E04-05A | Concentrated supernatant (C200) | 87.4 | 81.5 | 92.4 | 95.3 | 93.8 | 94.2 | 89.8 |
| MS043-E04-05A | Modified concentrated supernatant (C200H) | 100 | 100 | 100 | 91.7 | 92.5 | 90.7 | 94.3 |
| SD061-K07-05A | Modified concentrated supernatant (C200H) | 96.7 | 95.7 | 100 | 97.1 | 95.7 | 98.6 | 86.6 |
| SD062-L18-05A | Modified concentrated supernatant (C200H) | 98.8 | 89.0 | 97.9 | 100 | 94.1 | 100 | 100 |
| SD061-I26-06A | Supernatant heat treated then concentrated (C200HS) | 97.7 | 92.4 | 100 | 95.9 | 100 | 98.4 | 94.3 |
| SD062-K20-06A | Supernatant partially concentrated, then heat treated, then concentrated (C200HS) | 100 | 94.1 | 100 | 91.8 | 100 | 100 | 90.6 |
| SA027-K07-07A | Isoelectrically precipitated supernatant (C200IS) | 100 | 98.0 | 100 | 95.7 | 100 | 100 | 100 |

As can be seen from the results of Table IX, the dried isolates from modified concentrated supernatant (C200H), heat treated then concentrated supernatant (C200HS) and isoelectrically precipitated supernatant (C200IS), were notably more soluble in water at various pH values than the dried isolate from concentrated supernatant (C200) produced according to Example 1.

Example 5

This Example contains an evaluation of the solubility of the spray dried canola protein isolates produced in Examples 2 and 3 in a soft drink and a sports drink.

The solubility in a soft drink (Sprite) or a sports drink (Orange Gatorade) of the spray dried concentrated supernatant (C200) and modified products (C200H and C200HS) produced by the procedures of Example 2 and isoelectrically precipitated supernatant (C200IS) produced by the procedures of Example 3, were determined using a modification of the procedure of Morr et al., J. Food Sci. 50:1715-1718, as described above in Example 4 but with the soft drink or sport drink replacing the water, a protein concentration of 2% w/v and no pH adjustment performed.

The results obtained are set forth in the following Table X:

TABLE X

| Batch | Product | Solubility (%) in carbonated soft drink | Solubility (%) in non-carbonated sports drink |
|---|---|---|---|
| SA033-E10-04A | Concentrated supernatant (C200) | 91.5 | 85.2 |
| MS043-E04-05A | Concentrated supernatant (C200) | 94.2 | 84.8 |
| MS043-E04-05A | Modified concentrated supernatant (C200H) | 92.0 | 96.3 |
| SD061-K07-05A | Modified concentrated supernatant (C200H) | 99.3 | 97.0 |
| SD062-L18-05A | Modified concentrated supernatant (C200H) | 100 | 98.2 |
| SD061-I26-06A | Supernatant heat treated then concentrated (C200HS) | 100 | 98.7 |
| SD062-K20-06A | Supernatant partially concentrated, then heat treated, then concentrated (C200HS) | 97.3 | 95.6 |
| SA-077-K07-07A | Isoelectrically precipitated supernatant (C200IS) | 95.2 | 95.7 |

As can be seen from the results of Table X, the dried isolate from modified concentrated supernatant (C200H), heat treated then concentrated supernatant (C200HS) and isoelectrically precipitated supernatant (C200IS) were notably more soluble in a soft drink and a sports drink than the dried isolate from concentrated supernatant (C200).

Example 6

This Example contains an evaluation of the clarity in solution of the spray dried canola protein isolates produced in Examples 2 and 3 dissolved in water at various pH values.

Sufficient protein powder to supply 0.5 g of protein was weighed into a beaker and then a small amount of reverse osmosis (RO) purified water was added and the mixture stirred until a smooth paste formed. Additional water was then added to bring the volume to approximately 45 ml. The contents of the beaker were then slowly stirred for 60 minutes using a magnetic stirrer. The pH was determined immediately after dispersing the protein and was adjusted to the appropriate level (2, 3, 4, 5, 6 or 7) with NaOH or HCl. A sample was also prepared at native pH. For the pH adjusted samples, the pH was measured and corrected two times during the 60 minutes stirring. After the 60 minutes of stirring, the sample was made up to 50 ml total volume with RO water, yielding a 1% w/v protein dispersion. The clarity of the solutions was determined by measuring the absorbance at 600 nm with pure water used to blank the spectrophotometer. The lower the absorbance reading, the greater the clarity.

The results obtained are set forth in the following Table XI:

TABLE XI

| Batch | Product | A600 | | | | | | Native pH |
| --- | --- | --- | --- | --- | --- | --- | --- | --- |
| | | pH 2 | pH 3 | pH 4 | pH 5 | pH 6 | pH 7 | |
| SA033-E10-04A | Concentrated supernatant (C200) | 2.117 | 2.167 | 2.221 | 2.244 | 2.267 | 2.364 | 2.278 |
| MS043-E04-05A | Concentrated supernatant (C200) | 1.748 | 1.902 | 1.937 | 2.010 | 1.688 | 1.613 | 1.834 |
| MS043-E04-05A | Modified concentrated supernatant (C200H) | 0.185 | 0.210 | 0.237 | 0.493 | 0.518 | 0.722 | 0.610 |
| SD061-K07-05A | Modified concentrated supernatant (C200H) | 0.080 | 0.085 | 0.079 | 0.212 | 0.432 | 0.507 | 0.402 |
| SD062-L18-05A | Modified concentrated supernatant (C200H) | 0.047 | 0.049 | 0.046 | 0.050 | 0.306 | 0.553 | 0.058 |
| SD061-I26-06A | Supernatant heat treated then concentrated (C200HS) | 0.043 | 0.050 | 0.052 | 0.367 | 0.649 | 0.426 | 0.791 |
| SD062-K20-06A | Supenatant partially concentrated, then heat treated, then concentrated (C200HS) | 0.044 | 0.050 | 0.049 | 0.146 | 0.482 | 0.520 | 0.539 |
| SA077-K07-07A | Isoelectrically precipitated supernatant (C200IS) | 0.040 | 0.044 | 0.052 | 0.199 | 0.584 | 0.324 | 0.050 |

As can be seen from the results of Table XI, the dried isolate from modified concentrated supernatant (C200H), heat treated then concentrated supernatant (C200HS) and isoelectrically precipitated supernatant (C200IS) produced solutions with notably greater clarity in water at various pH values than the dried isolate from concentrated supernatant (C200). The difference was most pronounced at the low pH values.

Example 7

This Example contains an evaluation of the clarity in solutions of spray dried isolates produced in Examples 2 and 3 dissolved in a soft drink or a sports drink.

Clarity was assessed by measuring the absorbance of visible light at 600 nm by a solution of 2% w/v protein in a colourless, transparent, commercial carbonated soft drink (Sprite) or a coloured, commercial non-carbonated sports drink (Orange Gatorade). The spectrophotometer was blanked with a pure sample of the appropriate drink prior to measurement of the clarity of a protein containing sample. The lower the absorbance reading, the better light was being transmitted and the better the clarity of the solution.

The results obtained are set forth in the following Table XII:

TABLE XII

| Batch | Product | A600 in carbonated soft drink | A600 in non-carbonated sports drink |
| --- | --- | --- | --- |
| SA033-E10-04A | Concentrated supernatant (C200) | 2.716 | 2.808 |
| MS043-E04-05A | Concentrated supernatant (C200) | 2.248 | 2.514 |
| MS043-E04-05A | Modified concentrated supernatant (C200H) | 0.397 | 0.954 |
| SD061-K07-05A | Modified concentrated supernatant (C200H) | 0.099 | 0.363 |
| SD062-L18-05A | Modified concentrated supernatant (C200H) | 0.079 | 0.344 |
| SD061-I26-06A | Supernatant heat treated then concentrated (C200HS) | 0.081 | 0.326 |
| SD062-K20-06A | Supernatant partially concentrated, then heat treated, then concentrated (C200HS) | 0.092 | 0.311 |
| SA077-K07-07A | Isoelectrically precipitated supernatant (C200IS) | 0.040 | 0.168 |

As may be seen from the results of Table XII, the clarity of the solutions prepared from the spray dried isolate from modified concentrated supernatant (C200H), heat treated then concentrated supernatant (C200HS) and isoelectrically precipitated supernatant (C200IS) were far superior to those prepared from the spray dried concentrated supernatant (C200).

Example 8

This Example contains the pH values of common beverages.

The pH value of common beverages was determined by a pH meter and the results obtained are set forth in the following Table XIII:

TABLE XIII

| pH values of common beverages | |
| --- | --- |
| Beverage | pH |
| Coca Cola Classic | 2.68 |
| Diet Coke | 3.41 |
| 7-Up | 3.60 |
| Sprite | 3.24 |
| Mountain Dew | 3.10 |
| Canada Dry Ginger Ale | 2.85 |
| Iced Tea (tea flavoured drink) | 3.19 |
| Snapple Peach Iced Tea (contains natural tea) | 2.96 |
| Club Soda | 4.61 |
| Orange Gatorade | 2.98 |

TABLE XIII-continued pH values of common beverages

| Beverage | pH |
|---|---|
| Fruit Punch Gatorade | 3.05 |
| Lemon Lime Gatorade | 2.97 |
| Green Tea SoBe | 2.72 |
| apple juice (not from concentrate) | 3.62 |
| orange juice (from concentrate) | 3.91 |
| grape juice (from concentrate) | 3.20 |
| tropical juice blend (apple, orange, pineapple, passionfruit, mango) (from concentrate) | 3.77 |
| apple, orange, passionfruit juice blend (from concentrate) | 3.69 |
| fruit punch | 2.93 |
| cranberry cocktail | 2.77 |

Example 9

This Example contains a further evaluation of the solubility of the spray dried concentrated supernatant (C200), modified products (C200H and C200HS) and isoelectrically-precipitated supernatant (C200IS) produced by procedures of Examples 1, 2 and 3.

Sufficient protein powder to supply 0.5 g of protein was weighed into a beaker and then a small amount of reverse osmosis (RO) purified water was added and the mixture stirred until a smooth paste formed. Additional water was then added to bring the volume to approximately 45 ml. The contents of the beaker were then slowly stirred for 60 minutes using a magnetic stirrer. The pH was determined immediately after dispersing the protein and was adjusted to the appropriate level (2, 3, 4, 5, 6 or 7) with NaOH or HCl. A sample was also prepared at native pH. For the pH adjusted samples, the pH was measured and corrected two times during the 60 minutes stirring. After the 60 minutes of stirring, the samples were made up to 50 ml total volume with RO water, yielding a 1% w/v protein dispersion. Samples (20 ml) of the dispersions were then transferred to pre-weighed centrifuge tubes that had been dried in a 105° C. oven for 30 minutes then cooled in a desiccator and the tubes capped. The samples were centrifuged at 7800 g for 10 minutes, which sedimented insoluble material and yielded a clear supernatant. The supernatant and the tube lids were discarded and the pellet material dried overnight in an oven set at 55° C. The next morning the tubes were transferred to a desiccator and allowed to cool. The weight of dry pellet material was recorded. The dry weight of the initial protein powder was calculated by multiplying the weight of powder used by a factor of ((100−moisture content of the powder (%))/100). Solubility of the product was then calculated as:

$$\text{Solubility}(\%) = (1 - (\text{weight dry insoluble pellet material}/(\tfrac{2}{5} \times \text{initial weight dry protein powder}))) \times 100$$

The results obtained are set forth in the following Table XIV:

TABLE XIV

| Batch | Product | Solubility (%) | | | | | | |
|---|---|---|---|---|---|---|---|---|
| | | pH 2 | pH 3 | pH 4 | pH 5 | pH 6 | pH 7 | Nat. pH |
| SA034-J12-04A | Modified concentrated supernatant (C200H) | 99.0 | 97.7 | 96.0 | 97.2 | 87.5 | 89.5 | 89.9 |
| SA035-J14-04A | Concentrated supernatant (C200) | 96.2 | 95.7 | 96.0 | 93.3 | 86.2 | 87.5 | 86.7 |
| SA035-J14-04A | Modified concentrated supernatant (C200H) | 97.1 | 97.3 | 96.6 | 97.2 | 87.9 | 87.4 | 90.8 |
| SA033-E10-04A | Concentrated supernatant (C200) | 91.4 | 90.0 | 91.8 | 91.9 | 81.1 | 84.9 | 89.3 |
| MS043-E04-05A | Concentrated supernatant (C200) | 93.9 | 92.9 | 93.5 | 91.9 | 86.1 | 82.7 | 87.5 |
| SD061-K07-05A | Modified concentrated supernatant (C200H) | 98.8 | 97.6 | 97.4 | 95.3 | 91.0 | 93.3 | 94.8 |
| SD061-I26-06A | Supernatant heat treated then concentrated (C200HS) | 97.5 | 97.6 | 98.4 | 95.8 | 88.2 | 92.7 | 88.1 |
| SD062-K20-06A | Supernatant partially concentrated, then heat treated, then concentrated (C200HS) | 98.3 | 98.2 | 97.9 | 97.6 | 91.9 | 92.2 | 93.4 |
| SA07-K07-07A | Isoelectrically precipitated supernatant (C200IS) | 99.4 | 100 | 99.3 | 97.8 | 96.3 | 98.5 | 99.9 |

As can be seen from the results of Table XIV, the dried isolate from modified concentrated supernatant (C200H), heat treated then concentrated supernatant (C200HS) and isoelectrically precipitated supernatant (C200IS) were notably more soluble in water at various pH values than the dried isolate from concentrated supernatant (C200).

Example 10

This Example contains an evaluation of the heat stability at pH 7 of the spray dried concentrated supernatant (C200), modified product (C200H) and isoelectrically-precipitated supernatant (C200IS) produced by procedures of Examples 1, 2 and 3.

Sufficient protein powder to supply 1.6 g of protein was weighed into a beaker and then approximately 15 g of reverse osmosis (RO) purified water was added and the mixture stirred for a total of 60 minutes using a magnetic stirrer. As necessary, the product was also manually dispersed with a stirring rod as magnetic stirring proceeded. After 30 minutes of stirring the pH of the sample was determined and adjusted to 7 using NaOH or HCl as necessary. The sample was then stirred for an additional 30 minutes. After the 60 minutes of stirring, the pH was checked and readjusted to 7 if necessary then the sample was made up to 20 g total weight with RO water, yielding an 8% w/w protein dispersion. The dispersions were transferred to pre-weighed centrifuge tubes that had been dried in a 105° C. oven for 30 minutes then cooled in a desiccator. The weight of dispersion in the tubes was recorded and then the samples were capped and heat treated by placing them in a 90° C. water bath for 30 minutes. The water level was maintained higher than the sample liquid level throughout the heating process. After the heat treatment the samples were immediately cooled by placing them in an ice water bath. The samples were then placed in the refrigerator overnight. The next morning the samples were centrifuged three times each at 7800 g for 10 minutes. The supernatants were decanted from the tubes (note some minor losses of pellet material were observed for certain samples where completely compact pellets were not obtained) and the tube lids discarded. The pellet material was dried by placing the open tubes in a 55° C. oven overnight. The next morning the samples were transferred to the desiccator and allowed to cool. The weight of dried pellet material was measured. The dry weight of the initial protein powder was calculated by multiplying the weight of powder used by a factor of ((100−moisture content of the powder (%))/100). The effect of heat treatment on product solubility was then calculated as:

% of powder insoluble after heat treatment=(weight dry insoluble pellet material/weight dispersion in centrifuge tube/20)×initial weight dry protein powder))×100

The results obtained are set forth in the following Table XV:

TABLE XV

| Sample | % of initial powder insoluble after heat treatment |
|---|---|
| SA034-J12-04A C200 | 22.8 |
| SA034-J12-04A C200H | 12.3 |
| SA035-J14-04A C200 | 18.6 |
| SA035-J14-04A C200H | 12.7 |
| SA033-E10-04A C200 | 42.2 |
| SD061-K07-05A C200H | 14.6 |
| SA077-K07-07A C200IS | 5.8 |

As may be seen from the results of Table XV, the heat stabilities of the solutions prepared from the spray dried isolates from modified concentrated supernatant (C200H) and from isoelectrically precipitated supernatant (C200IS) were superior to those prepared from the spray dried concentrated supernatant (C200).

Example 11

This Example contains an evaluation of the heat stability at pH 6 of the spray dried concentrated supernatant (C200), modified products (C200H and C200HS) and isoelectrically precipitated supernatant (C200IS) produced by procedures of Examples 1, 2 and 3.

Sufficient protein powder to supply 0.3 g of protein was weighed into a beaker and then approximately 25 g of reverse osmosis (RO) purified water was added and the mixture stirred for a total of 60 minutes using a magnetic stirrer. After 30 minutes of stirring the pH of the sample was determined and adjusted to 6 using NaOH or HCl as necessary. The sample was then stirred for an additional 30 minutes. After the 60 minutes of stirring, the pH was checked and readjusted to 6 if necessary then the sample was made up to 30 g total weight with RO water, yielding a 1% w/w protein dispersion. The dispersions were transferred to pre-weighed centrifuge tubes that had been dried in a 105° C. oven for 30 minutes then cooled in a desiccator. The weight of dispersion in the tubes was recorded and then the samples were capped and heat treated by placing them in a 85° C. water bath for 10 minutes. The water level was maintained higher than the sample liquid level throughout the heating process. After the heat treatment, the samples were immediately cooled by placing them in an ice water bath. The samples were then centrifuged at 7800 g for 10 minutes. The supernatants were decanted from the tubes and the tube lids discarded. The pellet material was dried by placing the open tubes in a 55° C. oven overnight. The next morning the samples were transferred to the desiccator and allowed to cool. The weight of dry pellet material was measured. The dry weight of the initial protein powder was calculated by multiplying the weight of powder used by a factor of ((100−moisture content of the powder (%))/100). The effect of heat treatment on product solubility was then calculated as:

% of powder insoluble after heat treatment=(weight dry insoluble pellet material/((weight dispersion in centrifuge tube/30)×initial weight dry protein powder))×100

The results obtained are set forth in the following Table XVI:

TABLE XVI

| Sample | % of initial powder insoluble after heat treatment |
|---|---|
| SA034-J12-04A C200 | 19.6 |
| SA034-J12-04A C200H | 9.0 |
| SA035-J14-04A C200 | 27.5 |
| SA035-J14-04A C200H | 13.7 |
| SA033-E10-04A C200 | 30.4 |
| SD061-I26-06A C200HS | 8.9 |
| SA077-K07-07A C200IS | 4.5 |

As can be seen from the results of Table XVI, the heat stabilities of the solutions prepared from the spray dried isolate from modified concentrated supernatant (C200H), heat treated then concentrated supernatant (C200HS) and isoelectrically precipitated supernatant (C200IS) were superior to those prepared from the spray dried concentrated supernatant (C200).

Example 12

This Example contains an evaluation of the solubility at pH 3.5 and a salinity of 0.10M NaCl of spray dried concentrated supernatant (C200), modified product (C200H) and isoelectrically precipitated supernatant (C200IS) produced by the procedures of Examples 1, 2 and 3.

Sufficient protein powder to supply 0.5 g of protein was weighed into a beaker and then approximately 45 g of 0.1M NaCl was added. The contents of the beaker were stirred for 30 minutes using a magnetic stirrer. The pH was then adjusted to 3.5 by the addition of HCl. The sample was then stirred for an additional 30 minutes. At this time the pH was checked and readjusted to 3.5 if necessary then the sample weight was made up to 50 g with additional 0.1M NaCl, yielding a 1% w/w protein dispersion. Samples (approximately 30 g) of the dispersions were then transferred to pre-weighed centrifuge tubes that had been dried in a 105° C. oven for 30 minutes then cooled in a desiccator. The weight of dispersion in the tubes was recorded and the tubes capped. The samples were centrifuged at 7800 g for 10 minutes, which sedimented insoluble material. The supernatants were decanted from the tubes (note some very minor losses of pellet material were observed for certain samples where completely compact pellets were not obtained) and the tube lids discarded. The pellet material was dried overnight in an oven set at 55° C. The next morning the tubes were transferred to a desiccator and allowed to cool. The weight of dry pellet material was recorded. The dry weight of the initial protein powder was calculated by multiplying the weight of powder used by a factor of ((100−moisture content of the powder (%))/100). The effect of the pH and salt concentration on product solubility was then calculated as:

% powder insoluble under test conditions=(weight dry insoluble pellet material/((weight of initial sample in centrifuge tube/50)×initial weight dry protein powder))×100

The results obtained are set forth in the following Table XVII:

TABLE XVII

| Sample | % of initial powder insoluble in 0.1M NaCl at pH 3.5 |
|---|---|
| SA034-J12-04A C200 | 4.1 |
| SA034-J12-04A C200H | 1.4 |
| SA035-J14-04A C200 | 9.4 |
| SA035-J14-04A C200H | 2.6 |
| SA033-E10-04A C200 | 19.1 |
| SD061-K07-05A-C200H | 1.6 |
| SA077-K07-07A C200IS | 0.8 |

As can be seen from the results of Table XVII, the dried isolates from modified concentrated supernatant (C200H) and isoelectrically precipitated supernatant (C200IS) were notably more soluble in saline at pH 3.5 than the dried isolate from concentrated supernatant (C200).

Example 13

This Example contains an evaluation of the surface hydrophobicity of spray dried concentrated supernatant (C200), modified products (C200H and C200HS) and isoelectrically-precipitated supernatant (C200IS) produced by the procedures of Examples 1, 2 and 3.

The surface hydrophobicities of the different isolates were determined at room temperature using the surface hydrophobicity ($S_0$) test involving the hydrophobic dye: 1-aniline 8-naphthalene sulfonate (ANS). The relative fluorescence intensity was measured using a spectrofluorimeter with the hydrophobicity ($S_0$) for the proteins determined by calculation of the net relative fluorescence intensity (RFI) slope. The higher the $S_0$, the more hydrophobic the protein is, since the dye is attracted to hydrophobic sites on the protein molecule.

Since concentrated supernatant derived protein (C200) contains a higher percentage of globulin (7S), this isolate was found to contain greater hydrophobicity according to the ANS test. The canola globulins are considered to be quite hydrophobic and this was shown to be the case. The modified products produced lower values as expected with the reduced levels of globulin proteins. The main component of both isolates is the albumin napin. This protein is very polar resulting in a very low surface hydrophobicity.

The results are set forth in the following Table XVIII. The data is adjusted to reflect 100% (N×6.25) protein for each isolate.

TABLE XVIII

| Sample | % 7S | $S_0$ 100% N × 6.25 |
|---|---|---|
| SA033-E10-04A C200 | 32.18% | 78.1 |
| SA034-J12-04A C200 | 13.13% | 32.6 |
| SA035-J14-04A C200 | 24.52% | 58.1 |
| SA034-J12-04A C200H | 3.55% | 12 |
| SA035-J14-04A C200H | 7.55% | 14.9 |
| SD061-I26-06A C200HS | 4.05% | 12.1 |
| SA077-K07-07A C200IS | 3.12% | 17.6 |

As can be seen from the results of Table XVIII, the dried isolates from modified concentrated supernatant (C200H), heat treated then concentrated supernatant (C200HS) and isoelectrically-precipitated supernatant (C200IS) were notably less hydrophobic than the dried isolate from concentrated supernatant (C200). Furthermore, the results show that the surface hydrophobicity is linearly related to the content of globulins.

Example 14

This Example contains an evaluation of the absorbance at 280 nm of 1 mg/ml protein solutions of spray dried concentrated supernatant (C200), modified products (C200H and C200HS) and isoelectrically precipitated supernatant (C200IS) produced by procedures of Examples 1, 2 and 3.

Sufficient protein powder to supply 50 mg of protein was weighed into a beaker and then approximately 45 ml of 10 mM phosphate buffer, pH 6.66 was added and the mixture stirred for a total of 60 minutes using a magnetic stirrer. After the 60 minutes of stirring the sample was made up to 50 ml total volume with buffer, yielding a protein concentration of 1 mg/ml. The samples were clarified by centrifugation at 7800 g for 10 minutes then the supernatants were transferred to a quartz cuvette and the absorbance at 280 nm read using the phosphate buffer as a blank.

The results obtained are set forth in the following Table XIX:

TABLE XIX

| Sample | Absorbance at 280 nm |
|---|---|
| SA034-J12-04A C200 | 0.694 |
| SA034-J12-04A C200H | 0.656 |
| SA035-J14-04A C200 | 0.710 |
| SA035-J14-04A C200H | 0.654 |
| SA033-E10-04A C200 | 0.700 |
| SD061-I26-06A C200HS | 0.668 |
| SA077-K07-07A C200IS | 0.611 |

As may be seen from the results of Table XIX, the solutions prepared from the spray dried concentrated supernatant (C200) absorbed more strongly at 280 nm than the solutions prepared from modified concentrated supernatant (C200H), heat treated then concentrated supernatant (C200HS) and isoelectrically precipitated supernatant (C200IS).

SUMMARY OF DISCLOSURE

In summary of this disclosure, a novel canola protein isolate having an increased content of 2S protein and a reduced quantity of 7S protein is provided having utility in producing

What we claim is:

1. A process for the preparation of a canola protein isolate having an increased proportion of 2S canola protein, which comprises:
   (a) providing an aqueous solution of 2S and 7S proteins consisting predominantly of 2S protein,
   (b) isoelectrically precipitating 7S protein from the aqueous solution,
   (c) removing precipitated 7S protein from the aqueous solution, and
   (d) recovering a canola protein isolate having a protein content of at least 90 wt % (N×6.25) d.b. and having an increased proportion of 2S canola protein compared to the aqueous solution of 2S and 7S proteins.

2. The process of claim 1 wherein said isoelectric precipitation is effected under pH and salt conditions sufficient to precipitate at least 50 wt % of the 7S canola protein present in the aqueous solution.

3. The process of claim 2 wherein said isoelectric precipitation is effected under pH and salt conditions sufficient to precipitate at least 75 wt % of the 7S canola protein present in the aqueous solution.

4. The process of claim 1 wherein said isoelectric precipitation is effected by:
   (i) salinating the aqueous solution to a conductivity of at least 0.3 mS, and
   (ii) adjusting the pH of the salinated aqueous solution to a value of about 2.0 to about 4.0.

5. The process of claim 4 wherein said conductivity is about 10 to about 20 mS and said pH is about 3.0 to about 3.5.

6. The process of claim 1 wherein said aqueous solution of 2S and 7S canola proteins is supernatant, partially concentrated supernatant or concentrated supernatant from canola protein micelle formation and precipitation.

7. The process of claim 6 wherein said canola protein micelle formation is effected by:
   (a) extracting canola oil seed meal at a temperature of at least about 5° C. to cause solubilization of protein in said canola oil seed meal and to form an aqueous protein solution,
   (b) separating said aqueous protein solution from residual oil seed meal,
   (c) increasing the concentration of said aqueous protein solution to at least 200 g/L while maintaining the ionic strength substantially constant by a selective membrane technique to provide a concentrated protein solution,
   (d) diluting said concentrated protein solution into chilled water having a temperature of below 15° C. to cause the formation of the protein micelles, and
   (e) separating supernatant from settled protein micellar mass.

8. The process of claim 7 wherein said supernatant is concentrated to a protein concentration of about 100 to about 300 g/L prior to said isoelectric precipitation.

9. The process of claim 8 wherein said supernatant is concentrated to a protein concentration of about 200 to about 300 g/L.

10. The process of claim 8 wherein said concentration step is effected by ultrafiltration using at least one membrane having a molecular weight cut-off of about 3,000 to about 100,000 daltons.

11. The process of claim 10 wherein the concentrated supernatant resulting from ultrafiltration is subjected to diafiltration prior to said isoelectric precipitation.

12. The process of claim 11 wherein said diafiltration step is effected using from about 2 to about 20 volumes, preferably about 5 to about 10 volumes, of water, saline or acidified water using at least one membrane having a molecular weight cut-off of about 3,000 to about 100,000 daltons.

13. The process of claim 1 further comprising:
   (e) formulating said canola protein isolate as an aqueous beverage composition.

14. An aqueous solution of the canola protein isolate of claim 1.

15. The aqueous solution of claim 14 which is a canola protein isolate fortified beverage.

* * * * *